US00PP27165P2

(12) United States Plant Patent
Zaiger et al.

(10) Patent No.: US PP27,165 P2
(45) Date of Patent: Sep. 20, 2016

(54) INTERSPECIFIC TREE NAMED 'SWEET PIXIE 3'

(50) Latin Name: **Interspecific *Prunus* species**
Varietal Denomination: Sweet Pixie 3

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 81 days.

(21) Appl. No.: 14/544,662

(22) Filed: Feb. 2, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Tree being a regular and productive bearer of small size fruit.
3. Fruit with very good flavor and eating quality.
4. Fruit with attractive red skin color.
5. Fruit with good storage and shipping quality.

1 Drawing Sheet

Botanical designation: Interspecific *Prunus* species.
Variety denomination: 'SWEET PIXIE 3'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Sweet Pixie' Interspecific (U.S. Plant Pat. No. 23,211) and 'Sweet Pixzee 2' Interspecific (U.S. Plant Pat. No. 23,796).

STATEMENT REGARDING FEDERALLY SPONSORED RESEARCH AND DEVELOPMENT

Not applicable.

ORIGIN OF THE VARIETY

The new and distinct variety of interspecific tree consists of a combination of crosses between [(*Prunus salicina*×*Prunus avium*)×*Prunus avium*]. The present variety was selected as an open pollinated seedling from seed of 'Sweet Pixie' Interspecific (U.S. Plant Pat. No. 23,211). A large number of these open pollinated seedlings were budded onto older established trees of 'Nemaguard' Rootstock (non-patented) to induce earlier fruit production for evaluation. Under close and careful observation the present seedling exhibited desirable tree and fruit characteristics and was selected in 2008 for additional asexual propagation and commercialization.

ASEXUAL REPRODUCTION OF THE VARIETY

In 2008 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree which consists of [(Plum×Cherry)×Cherry] is of large size, vigorous, upright growth and is a regular and productive bearer of small size, yellow flesh fruit with very good flavor and eating quality. The fruit is further characterized by having attractive red skin color and firm flesh that has good shipping and storage quality. In comparison to its seed parent 'Sweet Pixie' Interspecific (U.S. Plant Pat. No. 23,211) the fruit of the new variety is approximately 16 days later in maturity. In comparison to the commercial variety 'Sweet Pixzee 2' Interspecific (U.S. Plant Pat. No. 23,796) the fruit of the new variety is 19 days later in maturity.

DESCRIPTION OF THE PHOTOGRAPH

The accompanying color photographic illustration shows typical specimens of the foliaga and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility of soil and climatic conditions.

*Form*.—Upright, usually pruned vase shape.

*Branching habit*.—Upright, crotch angle approximately 40°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 4 consecutive years. No alternate bearing observed.

*Fertility*.—Self sterile, pollinator required.

*Density*.—Medium dense, usually pruned to vase shape to increase air movement and sunlight to center of tree to enhance fruit color and health of fruit spurs.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium. Average circumference 50.8 cm at 25.4 cm above ground on a 6 year old tree.

*Stocky*.—Medium stocky.

*Texture*.—Medium shaggy, roughness increases with age.

*Color*.—Varies from 7.5YR 6/2 to 10YR 6/2.

Branches:

*Size*.—Medium. Average circumference 8.4 cm at 1.2 meters above ground. Crotch angle approximately 40°, increases with heavy crop load.

*Surface texture*.—New growth relatively smooth. Mature growth medium rough, roughness increases with age.

*Lenticels*.—Average number 53 in a 25.8 square cm area. Average length 3.5 mm. Average width 1.0 mm. Color varies from 2.5YR 4/10 to 5YR 5/8.

*Color*.—New growth varies from 5GY 6/6 to 5GY 5/6. Mature growth varies from 7.5YR 3/2 to 7.5YR 2/4, varies with age of growth.

Leaves:

*Size*.—Small. Average length 70.3 mm. Average width 32.0 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 18.5 mm. Average width 0.9 mm. Longitudinally grooved. Surface — glabrous. Color varies from 5GY 6/6 to 5GY 5/6.

*Glands*.—Type — globose. Size — small. Average length 0.1 mm. Average. diameter 0.1 mm. Average number 2, varies from 2 to 3. Located primarily on the base of leaf blade and upper portion of the petiole. Color varies from 5YR 3/4 to 5YR 3/6.

*Stipules*.—Average number 2. Average length 5.5 mm. Edges — pectinate. Color varies from 5YR 3/4 to 5YR 3/6.

*Color*.—Upper surface varies from 7.5GY 2/2 to 10GY 2/2. Lower surface varies from 5GY 3/2 to 7.5GY 3/2. Midvein color varies from 7.5GY 7/2 to 7.5GY 7/4.

Flower buds:

*Size*.—Medium to large. Average length 8.8 mm. Average width 4.7 mm.

*Hardiness*.—Hardy with respect to California winters.

*Density*.—Very dense.

*Form*.—Conical, becoming elongated just before opening.

*Pedicel*.—Size — medium to large. Average length 10.0 mm. Average width 0.6 mm. Surface glabrous. Color varies from 2.5GY 5/8 to 5GY 6/8.

*Color*.—N 9.5/ (white).

*Number of buds per spur*.—Average 9, varies from 6 to 11. Varies with age of spur.

Flowers:

*Blooming period*.—Date of First Bloom Mar. 2, 2014. Date of Petal Fall Mar. 10, 2014, varies slightly with climatic conditions.

*Size*.—Medium to large. Average height 11.7 mm. Average diameter 18.7 mm.

*Petals*.—Number — normally 5, alternately arranged to sepals. Size — medium to large. Average length 9.3 mm. Average width 6.2 mm. Form — elliptical. Margin — sinuate. Arrangement — free. Petal apex — rounded. Petal base — truncated. Color N 9.5/ (white). Both upper and lower surfaces glabrous.

*Sepals*.—Number — normally 5, alternately arranged to petals. Size — small to medium. Average length 2.6 mm. Average width 2.2 mm. Shape — triangular, apex rounded. Both upper and lower surfaces glabrous. Color — upper surface varies from 5GY 5/6 to 7.5GY 5/6. Lower surface varies from 5GY 6/6 to 5GY 5/6.

*Stamens*.—Average number per flower 30. Average filament length 9.0 mm. On average the stamens are above the height of the petals. Filament color N 9.5/ (white). Anther color varies from 5Y 8.5/8 to 5Y 8/8.

*Pollen*.—Self sterile, pollinator required. Color varies from 5Y 7/10 to 5Y 7/12.

*Pistil*.—Number — normally one. Surface glabrous. Average length 10.3 mm. Position of stigma even with the anthers. Color varies from 10Y 8/6 to 2.5GY 8/6.

*Fragrance*.—Heavy aroma.

*Color*.—N 9.5/ (white).

*Pedicel*.—Average length 12.6 mm. Average width 0.7 mm. Surface glabrous. Color varies from 2.5GY 6/8 to 5GY 5/8.

*Number flowers per flower bud*.—Average 2, varies from 1 to 3.

Fruit:

*Maturity when described*.—Firm ripe and ready for consumption.

*Date of first picking*.—Jul. 13, 2014.

*Date of last picking*.—Jul. 23, 2014, varies slightly with climatic conditions.

*Size*.—Small to medium. Average diameter axially 43.1 mm. Average transversely in suture plane 45.2 mm. Average weight 51.1 grams, varies slightly with fertility of the soil, amount of thinning and climatic conditions.

*Form*.—Globose.

*Suture*.—Slightly lipped, extends from base to apex.

*Ventral surface*.—Slightly lipped.

*Apex*.—Nearly rounded with slight point.

*Base*.—Flat.

*Stem cavity*.—Rounded to slightly elongated in suture plane. Average depth 3.4 mm. Average diameter 4.2 mm.

Stem:

*Size*.—Medium. Average length 17.4 mm. Average diameter 1.1 mm.

*Color*.—Varies from 10Y 6/6 to 2.5GY 7/8.

Flesh:

*Ripens*.—Evenly.

*Texture*.—Firm, crisp.

*Fibers*.—Few, small, tender.

*Firmness*.—Firm, comparable to commercial interspecific varieties.

*Aroma*.—Slight.

*Amydgalin*.—Undetected.

*Eating quality*.—Very good.

*Flavor*.—Very good, good balance between acid and sugar.

*Juice*.—Heavy amount, enhances flavor.

*Acidity*.—Not available.

*Brix*.—Average Brix 17.6°, varies slightly with amount of fruit per tree and climatic conditions.

*Color*.—Varies from 10YR 6/6 to 2.5Y 6/6.

*Pit cavity*.—Average length 21.6 mm. Average width 16.0 mm. Average depth 8.0 mm. Color varies from 10YR 6/8 to 10YR 5/8.

Skin:

*Thickness*.—Medium.

*Surface*.—Smooth.

*Bloom*.—Moderate amount.

*Tendency to crack*.—None.

*Color*.—Ground color varies from 2.5Y 8/6 to 5Y 7/6. Overspread with 7.5R 3/8 to 7.5R 2/6. Very small, randomly spaced areas of exposed ground color giving a speckling pattern to surface.

*Tenacity*.—Tenacious to the flesh.

*Astringency*.—Undetected.

Stone:

*Type*.—Clingstone, slight adherence to flesh.

*Size*.—Medium. Average length 18.7 mm. Average width 14.8 mm. Average thickness 6.9 mm.

*Form*.—Ovoid.

*Base*.—Flat.

*Apex*.—Pointed. Average length 0.7 mm.

*Surface*.—Slightly pitted throughout. One shallow groove on each side of suture extending from base toward apex.

*Sides*.—Unequal, one side extending further outward from suture plane.

*Ridges*.—Very narrow, small ridge near groove on each side of suture.

*Tendency to split*.—None.

*Color*.—Varies from 10YR 5/8 to 7.5YR 6/6 when dry.

Kernel:

*Size*.—Small. Average length 12.8 mm. Average width 8.7 mm. Average depth 4.4 mm.

*Form*.—Ovoid.

*Viability*.—Viable, complete embryo development.

*Skin color*.—Varies from 2.5Y 8/6 to 5Y 9/6.

Use: Dessert.

*Market*.—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

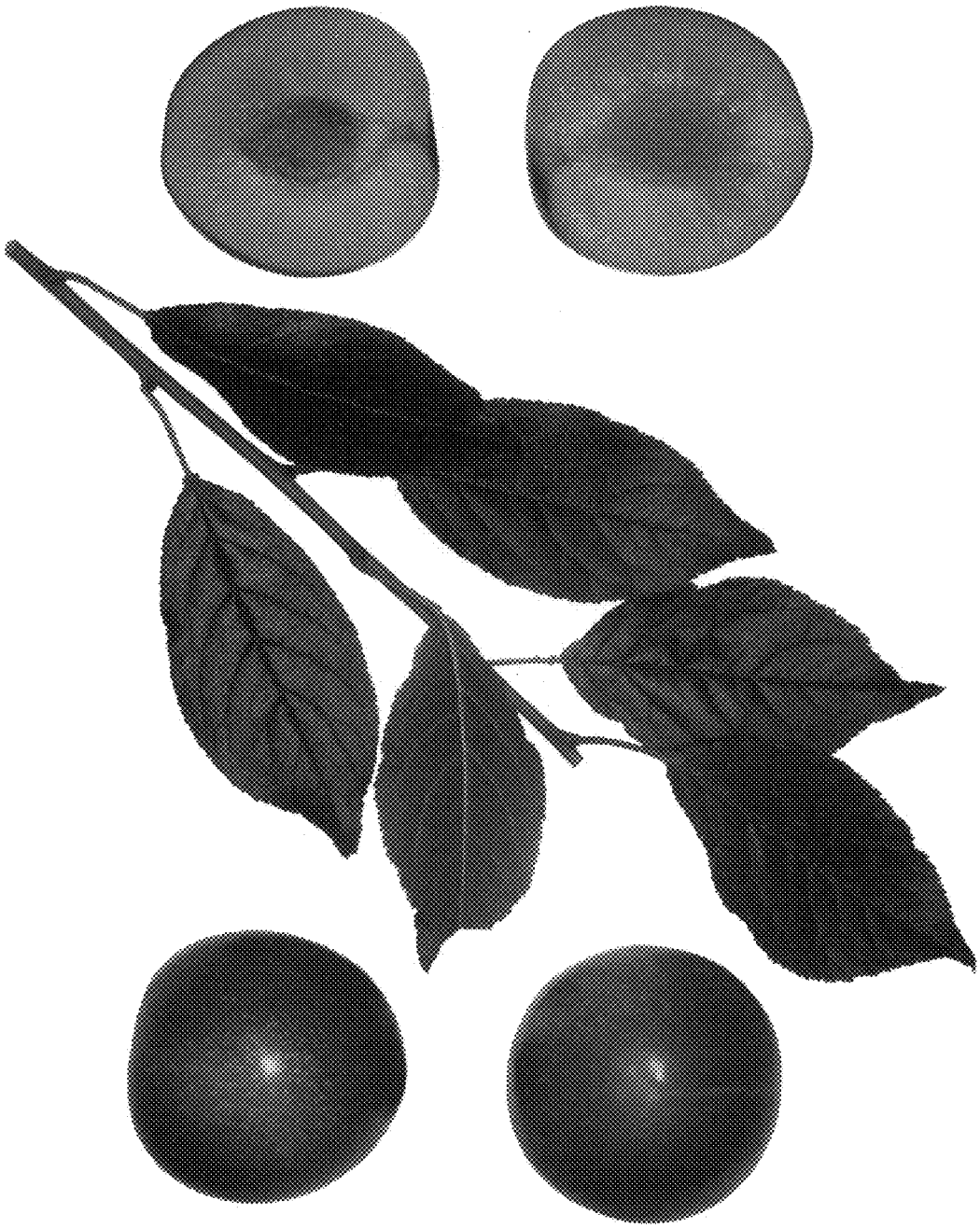

* * * * *